| (12) | United States Patent | (10) Patent No.: US 10,524,915 B2 |
|---|---|---|
| | Freeman et al. | (45) Date of Patent: Jan. 7, 2020 |

(54) THREE-DIMENSIONAL PRE-VASCULARIZED SCAFFOLD FOR BONE REGENERATION

(71) Applicants: Rutgers, The State University of New Jersey, New Brunswick, NJ (US); Virginia Commonwealth University, Richmond, VA (US)

(72) Inventors: Joseph Freeman, Piscataway, NJ (US); Brittany L. Taylor, Fredericksburg, VA (US); Pushpendra P. Patel, Fort Lee, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 12 days.

(21) Appl. No.: 15/534,857

(22) PCT Filed: Dec. 9, 2015

(86) PCT No.: PCT/US2015/064757
§ 371 (c)(1),
(2) Date: Jun. 9, 2017

(87) PCT Pub. No.: WO2016/094539
PCT Pub. Date: Jun. 16, 2016

(65) Prior Publication Data
US 2017/0360562 A1  Dec. 21, 2017

Related U.S. Application Data

(60) Provisional application No. 62/089,350, filed on Dec. 9, 2014.

(51) Int. Cl.
*A61F 2/28* (2006.01)
*A61K 9/70* (2006.01)
*A61F 2/30* (2006.01)

(52) U.S. Cl.
CPC .......... *A61F 2/28* (2013.01); *A61K 9/70* (2013.01); *A61F 2002/2825* (2013.01); *A61F 2002/30011* (2013.01); *A61F 2002/3024* (2013.01); *A61F 2002/30075* (2013.01); *A61F 2002/30224* (2013.01); *A61F 2310/00293* (2013.01); *A61F 2310/00365* (2013.01)

(58) Field of Classification Search
CPC .... A61F 2002/2825; A61F 2002/30011; A61F 2002/30075; A61F 2002/30224; A61F 2002/3024; A61F 2310/00293; A61F 2310/00365; A61F 2/28; A61K 9/70
See application file for complete search history.

(56) References Cited

U.S. PATENT DOCUMENTS

| 6,790,528 B2* | 9/2004 | Wendorff | D01D 5/0038 428/376 |
|---|---|---|---|
| 2002/0029084 A1 | 3/2002 | Paul et al. | |
| 2003/0021827 A1 | 1/2003 | Malaviya et al. | |
| 2004/0156878 A1* | 8/2004 | Rezania | A61L 27/38 424/423 |
| 2007/0255422 A1* | 11/2007 | Wei | A61F 2/28 623/23.51 |
| 2009/0018643 A1 | 1/2009 | Hashi et al. | |
| 2009/0148495 A1 | 6/2009 | Hammer et al. | |
| 2010/0233115 A1* | 9/2010 | Patel | A61L 15/26 424/78.08 |
| 2013/0253661 A1 | 9/2013 | D'Agostino et al. | |
| 2014/0227339 A1* | 8/2014 | Jackson | A61F 2/02 424/443 |
| 2014/0350692 A1* | 11/2014 | Jabbari | A61K 9/0024 623/23.58 |

FOREIGN PATENT DOCUMENTS

| JP | 2004243125 A | 9/2004 | |
|---|---|---|---|
| JP | 2009535101 A | 10/2009 | |
| WO | 2013169374 A1 | 11/2013 | |
| WO | 2014/075185 A1 | 5/2014 | |
| WO | WO 2014/075185 | * 5/2014 | ............ A61L 27/54 |

OTHER PUBLICATIONS

Of Wei et al. (Biomaterials 25 (2004) 4749-4757), (Year: 2004).*
Wei, G. et al., "Structure and Properties of Nano-Hydroxyapatite/Polymer Composite Scaffolds for Bone Tissue Engineering", Biomaterials (2004); vol. 25; pp. 4749-4757.

* cited by examiner

*Primary Examiner* — Anna R Falkowitz
(74) *Attorney, Agent, or Firm* — Fox Rothschild LLP

(57) ABSTRACT

The present invention provides scaffolds comprising dual structural organization for bone and regeneration. Methods for fabricating and using the scaffold are also disclosed.

27 Claims, No Drawings

THREE-DIMENSIONAL PRE-VASCULARIZED SCAFFOLD FOR BONE REGENERATION

CROSS-REFERENCE TO RELATED APPLICATIONS

This application claims the benefit of U.S. Provisional Application Ser. No. 62/089,350, filed Dec. 9, 2014, which is hereby incorporated by reference.

FIELD OF THE INVENTION

The present invention relates to the devices which mimic natural tissues and microstructures for bone repair and regeneration. There is also provided methods of fabricating the device and methods of implanting such device into a subject in need.

BACKGROUND OF THE INVENTION

Various bone diseases including bone injury and degeneration are a growing problem worldwide. A main challenge facing bone repair and regeneration is the difficulty of constructing devices with dual structural and functional organization similar to that of natural bone tissue. Two types of structures are present in bones, cortical and trabecular. The former is generally found surrounding the latter. Cortical bone is compose of highly compacted osteons which are oriented parallel to the longitudinal axis of the bone. The channel-like structure inside osteons provides a protecting space, also known as haversian canal, for the growth of vasculature and nerves. The high tensile and mechanical strength of the structure also prevents micro-crack propagation. Surrounded by cortical bone, trabecular bone has weaker mechanical strength but features an extensive network of pores which may vary significantly.

Different technologies and devices have been developed for bone repair and regeneration. However, many of them still have serious drawbacks. Autograft, a standard approach in orthopedic surgeries, is limited by supply and donor site morbidity. Although an alternative procedure using allograft overcomes the drawbacks of autograft, it still relates to issues such as more incidences of disease transmission and higher failure rate. More recently, various scaffolds have been developed for application in bone tissue engineering. However, most of the scaffolds do not have dual structural organization as found in natural bone tissue.

A need exists for biocompatible devices which not only provide the structural similarities to natural bones but also exhibit biological affinities suitable for tissue growth.

SUMMARY

The present invention provides biocompatible scaffolds suitable for bone repair and regeneration. The scaffolds contain channels mimicking the haversian systems of bone tissue and exhibit desirable mechanical properties and biological affinities. In particular, the scaffolds are characterized by the capabilities in promoting cell growth, osteoblastic differentiation and vascularization and maintaining long term viability and mechanical strength. The scaffolds hold the potential of replacing current methods for repairing complex, comminuted bone fractures, where the pieces of bone are pieced together with plates, pins, screws, and putty. This multiple pieces create instability and longer healing time because the cells have to travel through all of the different pieces to remodel the bone. Using the present invention, the pieces are completely removed and replaced with the scaffold for a simpler surgical procedure, increased mechanical stability, and a simpler, easier path for cells to produce new bone and vascular tissue.

In one aspect there is provided a scaffold for bone repair and regeneration comprising a plurality of fiber tubes and a fiber column, the latter enclosing the former. The enclosing column and the fiber tube have diameters within the physiological ranges of a cortical bone and an osteon, respectively.

In some embodiments, the scaffold further includes a cylindrical fiber core which is surrounded by the plurality of fiber tubes. The fiber core, mimicking a trabecular cone, is composed of the cross-linked hydrogel and a first polymer. The overall structure mimics the dual structural organization of natural bone with cortical and trabecular regions.

In order to provide sustained biocompatibility as well as desirable mechanical properties, the scaffold may further comprise one or more supporting posts cylinders around the fiber core. The cylinders or posts may also be placed around and/or within the fiber tubes. The cylinders or posts can be made from any suitable material such as ceramics. These cylinders or posts may also be composed of a type of calcium phosphate or a blend of several types. These types include hydroxyapatite (HPA), alpha tricalcium phosphate, beta tricalcium phosphate. In exemplary embodiments, the supporting posts composed of HPA, are distributed uniformly throughout the fiber tubes, which mimic osteons. Preferably, the posts have a diameter similar to an osteon.

The fiber tubes, fiber column, and fiber core are fabricated from fibers composed of a first polymer and a cross-linked hydrogel. The first polymer in the different fiber components may be the same or different. Likewise, the cross-linked hydrogel in the fiber tubes, fiber column, and fiber core may vary in each individual component.

Polymers of the scaffold components must meet requirements of mechanical strength and biological compatibility and affinity. Non-limiting examples of the first polymer include polycarbonate, polymethylmethacrylate, polyethylene, polyurethane, polyaryl etherketone, polyetheretherketone, polylactide, polyglycolide, poly(DL-lactide), poly(L-lactide), poly(ε-caprolactone), poly(dioxanone), poly(glyconate), poly(hydroxybutyrate), poly(hydroxyvalerate), poly(orthoesters), poly(carboxylates), poly(propylene fumarate), poly(phosphates), poly(carbonates), poly(anhydrides), poly(iminocarbonates), poly(phosphazenes) and copolymers, blends and combinations thereof.

The crossed-linked hydrogel reinforces the structural integrity of the fiber tube and fiber column. Crossed-linking also prevents water-soluble hydrogel from being washed away during mineralization. Non-limiting examples of suitable hydrogels include gelatin, alginic acid, hyaluronic acid, and poly(acrylic acid) hydrogel.

In some embodiments, at least one of the fiber column, fiber tubes, and fiber core further includes a second coating polymer. The coating polymer serves to aid with the sintering process to link various components of the scaffold together.

The scaffold of the present invention is also characterized by its bioactive nature. In some embodiments, the fiber tubes contain decellularized tissues such as blood vessels, which provide a network of decellularized vasculature and guide cells in the osteon-mimicking fiber tubes down a vascular lineage for the production of new blood vessels. Meanwhile, the levels of growth factors in these cells are low enough to avoid deleterious effects.

In some embodiments, the scaffold further contains seeded stems cells to become bone cells (osteoblasts) and blood vessel cells (vascular endothelial cells). The materials in the scaffold have the ability to convert stem cells (implanted or from neighboring, intact bone) into bone producing osteoblasts and blood vessel producing vascular endothelial cells.

The fiber angle relative to the longitudinal axis of the column also contributes to important mechanical properties. In some embodiments, the fiber of the enclosing column aligns in an angle of between 0 to 90 degrees to the longitudinal axis of the column. The fiber angle contributes to the compressive moduli and yield strength of the fiber column and can be readily adjusted.

In some embodiments, the angle ranges from about 15 to about 45 degrees.

In some embodiments, the angel is about 15 degrees. In some embodiments, the angle is random.

In some embodiments, the scaffold is mineralized. Mineralization enhances desirable mechanical properties of the scaffold with regards to yield stress and compressive modulus. Mineralized scaffolds also have better outcome with osteoblastic differentiation.

In some embodiments, the scaffold is heat sintered.

In another aspect there is provided a method of fabricating a scaffold for bone repair and regeneration. Generally, the method includes:

a) surrounding a fiber core with a plurality of fiber tubes;
b) enclosing the plurality of fiber tubes with a fiber sheet to form a column; and
c) sintering the column.

In some embodiments, the method further includes placing supporting posts uniformly around the fiber core and/or within the fiber tubes.

In some embodiments, the method further includes seeding and decellularizing a tissue in the fiber tubes. Preferably, the tissue is blood vessels.

In some embodiments, the method further includes seeding stem cells on to throughout the scaffold.

In some embodiments, the fiber tubes, fiber sheet, and fiber core each comprises a first polymer independently selected from the group consisting of polycarbonate, polymethylmethacrylate, polyethylene, polyurethane, polyaryletherketone, polyetheretherketone, polylactide, polyglycolide, poly(DL-lactide), poly(L-lactide), poly(ε-caprolactone), poly(dioxanone), poly(glyconate), poly(hydroxybutyrate), poly(hydroxyvalerate), poly(orthoesters), poly(carboxylates), poly(propylene fumarate), poly(phosphates), poly(carbonates), poly(anhydrides), poly(iminocarbonates), poly(phosphazenes), and copolymers, blends and combinations thereof. In some embodiments, the first polymer comprises PLLA.

In some embodiments, at least one of the fiber tubes, fiber sheet, and fiber core comprises a cross-linked hydrogel independently selected from the group consisting of gelatin, alginic acid, hyaluronic acid, and poly(acrylic acid) hydrogel.

In some embodiments, at least one of the fiber tube, fiber column, and fiber core further comprises a second coating polymer.

In some embodiments, the fiber of the enclosing sheet aligns in an angle of between 0 to 90 degrees to the longitudinal axis of the column.

In some embodiments, individual components including fiber tubes, fiber sheet, and fiber core can be mineralized before being assembled into a scaffold.

In some embodiments, the scaffold is mineralized before sintering, after sintering, or both.

A further aspect of the invention is a method of effecting bone repair or bone regeneration in a subject. The method comprises implanting or contacting the bone defect or area needing bone regeneration with a scaffold of the present invention. In some embodiments, the bone in need of repair or regeneration is cortical bone, trabecular bone, or both.

In another aspect there is provided a method of implanting the scaffold of the present invention, comprising the steps of:
a) creating a subcutaneous pocket; and
b) placing the scaffold into the pocket.

In some embodiments, the method include the steps of creating bone defect and placing the scaffold within the bone defect. In some embodiments, the method further includes seeding stem cells onto the scaffold stem cells prior to step a.

Details

Various embodiments provide scaffolds which mimic the dual structural organization of natural bone with cortical and trabecular regions. The scaffolds of the present invention are characterized by high surface area, high porosities, and interconnected pore networks. As a result, they not only demonstrate desirable mechanical properties but also facilitate cellular attachment and proliferation.

Throughout this patent document, various publications are referenced. The disclosures of these publications in their entireties are hereby incorporated by reference into this application in order to more fully describe the state of the art to which the disclosed matter pertains. While the following text may reference or exemplify specific components of a scaffold or steps of corresponding fabrication process, it is not intended to limit the scope of the invention to such particular reference or examples. Various modifications may be made by those skilled in the art, in view of practical and economic considerations, such as the source of the polymers and the characteristics of the scaffold. In order to more clearly and concisely describe the subject matter of the claims, the following definitions are intended to provide guidance as to the meaning of terms used herein.

Definition

The articles "a" and "an" as used herein mean "one or more" or "at least one," unless otherwise indicated. That is, reference to any element of the present invention by the indefinite article "a" or "an" does not exclude the possibility that more than one of the element is present.

"About" means the referenced numeric indication plus or minus 10% of that referenced numeric indication.

Scaffold and Components

In one aspect there is provided a scaffold for bone repair or regeneration comprising a plurality of fiber tubes and a fiber column enclosing the plurality of fiber tubes. To mimic the structure and characteristics of natural bones, the enclosing fiber column and the fiber tubes preferably have a diameter within the physiological range of a cortical bone and an osteon, respectively. In some embodiments, the scaffold also includes a cylindrical fiber core surrounded by the fiber tubes. The fiber tubes and the fiber core mimic the cortical bone and the trabecular bone respectively in a natural bone. The fiber tubes serve to guide vessel development and allow various factors to travel between the developing bond and blood vessels.

In some embodiments, the scaffold further includes supporting posts to bear the loads placed on the scaffold and ensure that appropriate properties be reached. The posts may be distributed uniformly throughout the section where the fiber tubes are placed or around the fiber core. A preferred material for the supporting posts is HAP (hydroxyapatite). Other minerals or polymers may also be incorporated to fine tune the strength of the posts. Utilization of the supporting posts in the scaffold overcomes issues such as mismatched strength, lack of bonding, and lack of degradation associated with traditional devices.

The fiber tubes of the scaffold may contain decellularized tissues, which have been reported in various types of tissue-engineering (see for example, Hoenicka, et al., Development Of Endothelium-Denuded Human Umbilical Veins As Living Scaffolds For Tissue-Engineered Small-Calibre Vascular Grafts. J. Tissue Eng. Regen. Med. 2013 April; 7(4):324-36; Lee, et al., Scaffold Technologies For Controlling Cell Behavior In Tissue Engineering. Biomed Mater. 2013 February; 8(1):010201). Suitable tissues for the present invention include blood vessels such as human saphenous vein and human umbilical vein endothelial cells (HUVEC). Incorporation of decellularized cells into the fiber tubes allows for blood to travel through the scaffold after implantation for nutrient transport to developing tissue.

Stem cells can also be incorporated into the scaffold for differentiating into multiple cellular lineages. Various types of stem cells are reported in the literature for tissue engineering (see for example, Li et al., Sustained Release of Bone Morphogenetic Protein 2 via Coacervate Improves the Osteogenic Potential of Muscle-Derived Stem Cells. Stem Cells Transl. Med. September 2013; 2(9): 667-677). Stem cells suitable for the present invention, including for example muscle-derived stem cells (MDSCs), adipose derived stem cells, and mesenchymal stem cells (MSCs) can be allogeneic or native. Stem cells can be populated throughout the scaffold, including the fiber tubes and fiber core, or in a particular section of the scaffold.

Selection of the materials for fabrication of the scaffold components must meet mechanical requirements with suitable high tensile and compressive properties. Meanwhile, to promote migration and proliferation of the cells and tissue formation within the scaffold, the materials should facilitate the formation of a network with suitable pore size, porosity, and pore interconnectivity which represent critical biological aspect of bone structure. To maintain suitable mechanical strength, the scaffold contains at least about 7%, 9%, 11%, 13%, or 15% of HPA. The addition of HPA supporting posts further increases the scaffold's strength.

Various materials can be used for the fabrication of the fiber tube, fiber column and fiber core. In some embodiments, the fiber tube, fiber column, and fiber core is each independently composed of a first polymer and a cross-linked hydrogel. Non-limiting examples of the first polymer include reinforced polymers, nylon, polycarbonate, polymethylmethacrylate, polyethylene, polyurethane, polyaryl etherketone, polyetheretherketone, polylactide, polyglycolide, synthetic or natural collagen, poly(DL-lactide), poly(L-lactide), poly(ε-caprolactone), poly(dioxanone), poly(glyconate), poly(hydroxybutyrate), poly(hydroxyvalerate), poly(orthoesters), poly(carboxylates), poly(propylene fumarate), poly(phosphates), poly(carbonates), poly(anhydrides), poly(iminocarbonates), poly(phosphazenes), and co-polymers, blends and combinations thereof. The first polymer and the cross-linked hydrogel in different components of the scaffold can be the same or different.

Cross-linked hydrogel enhances desirable properties of the scaffold and prevents it from mineralization process. In addition, the hydrogel coating may contribute to the porosity which affects the tissue growth and cell proliferation.

Hydrogels including various types of collagen and denatured collagen are available from natural sources or artificial means, including for example polypeptide-based hydrogels, polysaccharide-based hydrogels, and petrochemical-based hydrogels. The various types of hydrogels can be used individually or in combination with each other for fabricating components of the scaffold. Commonly used hydrogels includes gelatin, alginic acid, hyaluronic acid, and poly(acrylic acid) hydrogel. In some embodiments, the hydrogel is gelatin.

The hydrogel can be cross-linked by various agents. The resulting cross-linked hydrogel may impart physical and chemical properties suitable for scaffold fabrication and subsequent bone tissue growth. Non-limiting examples of cross-linking agents include glutaraldehyde, poly(ethylene glycol diacrylate (PEGDA), poly(ethyelene glycol) diglycidyl ether, 1-ethyl-3-(3-dimethylaminopropyl) carbodiimide, divinyl sulfone, and derivatives thereof. The cross-linking agent, for example 1-ethyl-3-(3-dimethylaminopropyl) carbodiimide, includes its corresponding salt such as hydrochloride salt. The amount of hydrogel and the extent of cross-linking depend on various factors such the fiber material and the specific component of the scaffold. Methods of cross-linking hydrogels are readily available in the literature and can be practiced without undue experiments (see for example, Nilimanka, International Journal of Pharmacy and Pharmaceutical Sciences, 2013, 5(4), 55-58; Hennink et al., Adv. Drug Deliv. Rev. 2002 January 17; 54(1):13-36). In some embodiments, the cross-lining agent is glutaraldehyde.

Because the scaffold is constructed from individual components, it is necessary that the fiber tubes, fiber column, and fiber core form a compact and inter-connected structure. Accordingly, each component preferably also includes sites for bonding with other components during the fabrication process. In some embodiments, one or more of the fiber tubes, fiber column, and fiber core further includes a second coating polymer which serves to link up different components during heat sintering process. Preferably, the second polymer has a melting point lower than that of the first polymer and does not decrease the mechanical strength and physical properties of the scaffold components. In some embodiments, the second coating polymer is Poly(D-lactide).

The ratio between the first polymer, second polymer, and the cross-linked hydrogel may vary depending on such factors as the type of the polymer and hydrogel, the specific bone to be repaired or regenerated, and the technique used for scaffold fabrication. In exemplary embodiments, the ratio between the first polymer and the hydrogel by weight includes: about 20:1, about 15:1, about 10:1, about 5:1, and about 1:1. In exemplary embodiments, the ratio between the first polymer and the second polymer by weight includes: about 10:1, about 5:1, about 3:1, about 1:1, about 1:3, about 1:5, and about 1:10. Additional ingredients which facilitate the formation of inter-connected network for the scaffold or enhance desirable mechanical and or biological properties may also be added to the scaffold components.

The fiber angle in the column of the scaffold contributes to mechanical properties including yield stress and compressive modulus. When the fiber in the column aligns 0° or 90° to the longitudinal axis of the scaffold, the weakest mechanical properties are observed. When the fiber angle is 15°, 30°, or 45°, the column demonstrates increased yield strength and young's modulus are observed. In exemplary embodiments of the scaffold, the fiber angles include: about 10°, 15°, 20°, 25°, 30°, 35°, 40°, 45°, 50°, 55°, 60°, 65°, 70°, 75°, 80°, and 85°.

Method of Scaffold Fabrication

A. Fabrication of Fiber Tubes

Fiber tubes may be fabricated by electrospinning a suitable polymer onto a core filler, which can be removed afterwards to form hollow channels mimicking haversian systems of bone tissue.

The core filler may be prepared by various techniques including for example, electrospinning a suitable material to a rotating mandrel. The resulting electrospun mat is then cut and rolled into thick fiber as a core filler. A mixture including a solution of a first polymer and a solution of a hydrogel is next electrospun to the core filler, followed by electrospinning a second coating polymer solution on top of the first polymer/hydrogel layer.

The first polymer, hydrogel, and the second coating polymer are as described above. The ratio among the first polymer, second polymer, and the cross-linked hydrogel may vary depending on factors including the type of the polymer and hydrogel, the specific bone to be repaired or regenerated, and the technique used for scaffold fabrication. One of ordinary skill in the art can readily determine the suitable amount of each agent without undue experiments in view of the specific source of material and needs of the scaffold. In some embodiments, the first polymer is poly(L-lactide) (PLLA), the hydrogel is gelatin, and the second coating polymer is poly(D-lactide) (PDLA).

Cross-linking of the hydrogel in the fiber tube can be accomplished by any suitable means. For example, the fiber tube may be dipped into a solution of a cross-linking agent or exposed to a vapor of the cross-linking agent. The condition (e.g. concentration, temperature, length) of the cross-linking step depends on the specific hydrogel, crossling agent, and desirable extent of cross-linking. In some embodiments, the fiber tube is exposed to the vapor of glutaraldehde. In some embodiments, the time of cross-linking is: about 5 minutes, about 30 minutes, about 45 minutes, about 1 hour, about 2 to 10 hours, about 5 to 15 hours, about 2 to 17 hours.

The core filler may be removed by biological, chemical, physical means. For example, a core fiber composed of biodegradable polymer will be suitable for constructing fiber tubes if biodegradation is completed within a desirable period of time. The core filler may also be removed by dissolving the core material in suitable solvents and washing it out to form a hollow channel. In exemplary embodiments, the core filler is composed of poly(ethylene oxide) (PEO) which be easily dissolved out in aqueous condition to create biomimetic haversian channels inside of the osteon scaffolds.

Mineralization contributes not only to the bio-viability of the scaffold but also its mechanical properties. Accordingly, in some embodiments, the fiber tubes are pre-mineralized. Premineralization treatment provides mineral seed for future mineral deposition and also serves to remove the core filler. In exemplary embodiments where the core filler is soluble, premineralization with aqueous solution of salts also wash away the filler to create hollow channels. Non-limiting examples of salts for premineralization includes sodium chloride, potassium chloride, calcium chloride, and magnesium chloride.

B. Fabrication of the Fiber Core

The fiber core can be similarly fabricated as above described for fiber tubes. However, because the fiber core is supposed to mimick the porous trabecular bone section, additional steps may be adopted to provide or modify the porosity on the fiber material. A non-limiting exemplary procedure includes the following steps: electrospin poly L-lactic acid (PLLA) and gelatin with salt crystals to obtain crystal-embedded electrospun mat; electronspin a additional thin layer of poly D-L lactic acid fiber on the mat; remove the crystals by leaching to create pores; cut the resulting mat into circular shapes and stack them into a cylinder; sinter the cylinder to provide a fiber core. Alternatively, the cylinder can be built up by rolling a small mat into a column and enclosing the column with additional bigger columns with incremental diameters.

C. Fabrication of the Supporting Posts

The supporting posts can be prepared by one or more suitable biocompatible materials. The length and shape may vary depending on the specific types of bone to be repaired or re-generated. In some embodiments, the diameter of the posts is approximately that of a osteon. In a non-limiting exemplary procedure, powdered hydroxyapatite is tightly packed in a cylindrical mold with water and held under a pre-determined pressure for a certain period of time. The resulting column is then sintered at an elevated temperature for an extended period of time.

D. Fabrication of the Enclosing Sheet

Enclosing sheets can be fabricated by eletrospinning a second coating polymer onto a rotating mandrel. A mixture of a first polymer solution and a hydrogel solution is next electrospun onto the layer of the coating polymer. Depending on the desirable characteristics and intended application of the enclosing sheet, another layer of the second coating polymer may be optionally electrospun onto layer of the first polymer/hydrogel.

The hydrogel in the enclosing sheet is cross-linked under suitable conditions which can be determined by one of ordinary skill in the art without undue experiments.

The first polymer, second polymer, and hydrogel are as described above. The fiber tube and the enclosing sheet may have same or different first polymer, same or different second coating polymer, and same or different hydrogel.

The enclosing sheet may be pre-mineralized under conditions described above. Premineralization may affect the mechanics by increasing the overall amount of mineral in the scaffolds.

E. Scaffold Fabrication

Scaffolds can be fabricated to mimick the structure of cortical bones or a system of cortical bones and trabecular bones. Cortical bone-like scaffolds are generally fabricated by wrapping multiple fiber tubes with an enclosing sheet to form a column. A dual-structure system of cortical bones and trabecular bones can be constructed by further aligning the fiber tubes around a fiber cylindrical core.

In some embodiments, scaffold fabrication includes the following steps:

a) surrounding a fiber core with a plurality of fiber tubes;
b) enclosing the plurality of fiber tubes with a fiber sheet to form a column; and
c) sintering the column;

wherein said fiber tube, fiber core and fiber sheet each comprises a cross-linked hydrogel, a first polymer, and optionally a second coating polymer. The first polymer, second polymer, and hydrogel are as described above.

In some embodiments, the method further includes placing one or more supporting posts around the fiber core in step a, wherein the supporting posts contain HPA. The quantity and location of the posts depend on the specific site and bones to be regenerated. In some embodiments, the posts are distributed uniformly in the section where the fiber tubes are located. Alternatively, the posts can be placed around the circumference of the fiber core.

In some embodiments, the method further includes seeding a tissue into the fiber tubes. Suitable tissues include blood vessel cells such as HUVEC. After the cells grow into organized vessels, a decellularization step is undertaken.

In some embodiments, stem cells are seeded on to the scaffold prior to the implantation step. Specific procedures for seeding cells are well known in the literature and can be performed by one of ordinary skill in the art with undue experiments.

In the absence of a fiber core at the center of the column, the scaffold mimics a cortical bone. In some embodiments, the fiber tubes of the column are aligned around a cylindrical fiber core which comprises a first polymer and a hydrogel. The resulting scaffold bears similarities structurally and functionally to a system of cortical bones and trabecular bones.

Heat sintering can be performed at different temperatures with different lengths of time, depending on the type of the polymer and desirable characteristics of the scaffold. In some exemplary embodiments, the sintering takes place a temperature of about 40° C., about 45° C., about 50° C., about 55° C., about 60° C., about 65° C., about 70° C., about 75° C., about 80° C., about 85° C., or about 90° C. The length of time for sintering can be about 15 minutes, about 30 minutes, about 45 minutes, about 60 minutes, or over about 90 minutes.

The length and width of the enclosing fiber sheet can be adjusted so that the fabricated scaffold will suit the size of the bones to be repaired or regenerated. Likewise, the diameter of the fiber tube should also be within the physiological range of the osteons. In exemplary embodiments, the diameter of the fiber tube is about 1 mm and the diameter of the fiber core is about 4 mm so that the final column has a diameter of about 6 mm, which translates to about a 2:1 ratio of trabecular to cortical section. In some embodiments, the ratio between the trabecular section and the cortical section is about 3:1, 5:2, 5:3, 7:3, or 7:4.

The enclosing sheet may be cut from different angles before being wrapped around the fiber tubes so that the fiber of the sheet is in a particular angle to the longitudinal axis of the resulting column. Varying fiber angle leads to different mechanical strength of the scaffold. In some embodiments, the enclosing sheet is cut and wrapped around the fiber tubes in a way that the fiber therein has a fiber angle of about 10°, 15°, 20°, 25°, 30°, 35°, 40°, 45°, 50°, 55°, 60°, 65°, 70°, 75°, 80°, or 85°. In some embodiments, the fiber angle is random and does not have to follow any specific pattern. In some embodiments, one or more columns may have mixed angles.

In some embodiments, the scaffold is further mineralized. Mineralization comprises incubating the scaffold in a solution of one or more salts, at room temperature or at an elevated temperature. Non-limiting example of salts include NaCl, KCl, CaCl, MgCl$_2$, and NaH$_2$PO$_4$. The time of incubation can be about 30 minutes, about 1 hour, about 2 hours, about 5 hours, about 12 hours, about 16 hours, about 24 hours, about 36 hours, about 48 hours, or more than 48 hours.

Various buffering agents may also be included in the solution for mineralization. Buffering agents suitable for use with the present invention include, for example, phosphates, such as sodium phosphate; phosphates monobasic, such as sodium dihydrogen phosphate and potassium dihydrogen phosphate; phosphates dibasic, such as disodium hydrogen phosphate and dipotassium hydrogen phosphate; citrates, such as sodium citrate (anhydrous or dehydrate); bicarbonates, such as sodium bicarbonate and potassium bicarbonate may be used. In some embodiments, a single buffering agent, e.g., a dibasic buffering agent is used. In some embodiments, a combination of buffering agents is employed, e.g., a combination of a tri-basic buffering agent and a monobasic buffering agent.

Method for Bone Repair or Regeneration

In another aspect there is provided a method for bone repair or regeneration comprising the implantation of the scaffold of the present invention. The size and length of the scaffold to be used can be determined by one of ordinary skill in the art without undue experiment in view of the specific condition of a subject.

Method for Implanting a Scaffold

In another aspect there is provided a method for implanting a scaffold to a subject in need bone repair, comprising the steps:

a) creating a subcutaneous pocket on a patient; and
b) placing the scaffold of claim 1 into the pocket.

Alternatively, the method may include the steps of creating bone defect and placing the scaffold within the bone defect. A bone defect or a pocket may be any form or any shape of physical change in the bone. In some embodiments, the method further includes seeding onto the scaffold stem cells. Suitable stem cells include, for example, muscle-derived stem cells (MDSCs) and mesenchymal stem cells (MSCs).

EXAMPLE

Example 1

Electrospinning

Poly (L-lactide) (PLLA) (inherent viscosity=2.0 dl/g, Mw=152,000) was purchased from Sigma Aldrich (St. Louis, Mo., USA). Poly (D,L-lactide) (PDLA) (inherent viscosity 0.6-0.8 dL/g) was purchased from SurModics Pharmaceuticals (Birmingham, Ala., USA). Dichloromethane (DCM), tetrahydrofuran (THF), and dimethylformaldehyde (DMF) were purchased from Fisher Scientific (Pittsburgh, Pa., USA). Gelatin, type A, from porcine skin was purchased from Sigma Aldrich (St. Louis, Mo., USA). NaCl, KCl, CaCl 2H$_2$O, MgCl$_2$ 6H$_2$O, NaHCO$_3$, and NaH$_2$PO$_4$ were purchased from Fisher Scientific (Pittsburgh, Pa., USA).

The electrospinning solutions were prepared by dissolving PLLA to 7% w/v in 75% DCM and 25% DMF, and dissolving PDLA to 22% w/v in 75% THF and 25% DMF. The PLLA/gelatin mixture was made by dissolving gelatin in 1 ml deionized (dl) water and adding it to the 7% PLLA solution. The amount of gelatin in solution was equal to 10%, w/w of the amount of PLLA in the solution. As two solutions are not miscible, they were vortexed for 1 hr to mix before electrospinning. Polymer solutions were made in 16 ml batches and to make overall volume of the gelatin/PLLA and PLLA solutions equal, 1 ml of DCM is replaced with 1 ml of gelatin.

First, the PDLA solution was loaded into a 5 ml plastic syringe with an 18-gauge needle and extruded at a rate of 5 mL/h. PDLA was electrospun on a rotating (2000 RPM) 5 cm diameter mandrel for a total volume of 1 ml, at a distance of 15 cm, with voltages of +12 kV and −5 kV applied. The gelatin/PLLA was then electrospun directly onto the PDLA layer with a working distance of 5 cm. The voltages applied were +18 kV and −7 kV. An additional layer of 1 ml PDLA was electrospun on top of gelatin/PLLA layer.

Poly (ethylene oxide) was dissolved in 10% ethanol to 10% w/v solution. The solution was electrospun onto a rotating mandrel with 5 cm diameter at rate of 5 ml/hr and working distance of 10 cm. A total volume of 3 ml was electrospun with voltages +10V and −3V. The electrospun mats were cut into 3 mm wide strips and rolled into fibers that were used for the next step.

Individual osteon-like scaffolds were electrospun onto rotating PEO fibers using the set up previously reported (Andric et al., Materials Science & Engineering C-Materials for Biological Applications 2011; 31:2). The fibers were placed into set up and placed in front of the negatively charged target. The PLLA/gelatin mixture was electrospun first to total volume of 1.5 ml, with the following parameters: working distance of 5 cm, at an extrusion rate of 5 ml/hr, and voltages of +17V and −9V. This was followed by electrospinning of the PDLA solution in total volume of 0.5 ml with the following parameters: working distance of 15 cm, extrusion rate of 5 ml/hr, and voltages of +13 V and −8V. Gelatin in all of the scaffolds was cross-linked in vapor of 2.5% glutaraldehyde for 2 hours.

Heat Sintering of Scaffolds

The complete scaffolds were assembled by heat sintering the individual components together at 54° C. for 45 min. Electrospun mats were cut into 1.2 cm strips and rolled to 4 mm segments and heat sintered. Osteon-like scaffolds were cut into small segments and placed around the core and everything was wrapped with an electrospun sheet. The final design consisted of a "trabecular" core that was 4 mm wide, surrounded by osteon-like segments and wrapped with an electrospun sheet to a final diameter of 6 mm. This provided a 2:1 ratio of trabecular to cortical section.

Mineralization of Scaffolds

All of the scaffolds were mineralized using a previously reported method by incubation in 10×SBF (Tas et al., Journal of Materials Research 2004; 19:2742). Briefly, a stock solution was made using NaCl, KCl, $CaCl\ 2H_2O$, $MgCl_2\ 6H_2O$, and $NaH_2PO_4$, and stored at room temperature. Prior to the mineralization process, $NaHCO_3$ was added while stirring vigorously, resulting in the following ion concentrations: $Ca^{2+}$ 25 mM, $HPO_4^{2-}$ 10 mM, $Na^+$ 1.03 M, $K^+$ 5 mM, $Mg^{2+}$ 5 mM, $Cl^-$ 1.065M, and $HCO_3^-$ 10 mM. The electrospun scaffolds were incubated in 200 ml of 10×SBF for 6, 24, and 48 hours at room temperature, with mineralizing solution replaced every 2 hours. After being removed from 10×SBF, all the samples were rinsed in dI water to remove mineral not attached to scaffolds, and vacuum dried overnight.

For the scaffolds with premineralization treatment, individual osteons and electrospun sheets were mineralized for 1 hour, and then rinsed in dI water and vacuum dried overnight. The electrospun pieces were then heat sintered as described above.

Alizarin Red Staining

Mineral deposition and distribution were characterized by the alizarin red stain. The scaffolds were cut into 200 μm section using a Cryostat HM 550 (Thermo Scientific Microm, Walldorf, Germany), rinsed in dI water and dried overnight. The scaffold sections were then stained with 40 mM Alizarin red solution for 10 min. The scaffolds were then washed with dI water five times and imaged using a stereoscope (Vision Engineering, New Milford, Conn., USA). Scaffolds from the cell study were fixed in 70% ethanol for 1 hr, rinsed in dI water and the same protocol described above was followed.

Mechanical Properties

The scaffolds were mechanically tested in compression using an Instron 5869 with Bioplus Bath (Norwood, Mass., USA). The tests were performed in phosphate buffered saline (PBS) (pH=7.4) at 37° C. Three mineralization times were investigated 6, 24 and 48 hr, and six samples per each group were tested (n=6). The 12 mm×6 mm (2:1 height to diameter ratio) scaffolds were tested in compression until failure with a uniform strain rate of 1.2 mm/min (10% stain/min). The data was analyzed to determine yield stress and compressive modulus.

Mineral Ash Weights

To quantify the amount of mineral on scaffolds, the polymer was burned off to determine mineral ash weight. After the initial weight of the samples was recorded, the samples were placed in ceramic crucibles, and placed in a high temperature furnace (Model FD1535M, Fisher Scientific, Pittsburgh, Pa., USA) at 700° C. for 24 hours. After cooling down, the mineral ash weight was recorded and the average mineral percent deposition calculated as ratio of mineral ash weight to samples original weight. Three samples per group were tested (n=3).

Cell Study

Mouse pre-osteoblastic cells (MC3T3-E1, ATCC) were cultured in Alpha Minimum Essential Medium (α-MEM, Cellgro, Mediatech, Manassas, Va., USA) supplemented with 10% fetal bovine serum (FBS, Cellgro, Mediatech, Manassas, Va., USA) and 1% streptomycin/penicillin (Cellgro, Mediatech, Manassas, Va., USA). The scaffolds were cut into 450 μm sections with a Cryostat HM 550 (Thermo Scientific Microm, Walldorf, Germany), soaked in DI water overnight and vacuum dried. The scaffolds were then secured into 24-well Ultra-Low Cluster plates (Costar) using Silastic Medical Adhesive (Dow Corning, Midland, Mich., USA) and were sterilized in 70% ethanol for 30 minutes followed by exposure to UV light for 30 minutes. The scaffolds were then washed with PBS and soaked in cell culture medium overnight.

Two groups of scaffolds were used, scaffolds mineralized for 24 hr (Min24) and scaffolds that were not mineralized (Min0). Approximately 100,000 cells were seeded onto each scaffold and were allowed to attach for one hour before adding culture medium to a final volume of 1 ml. After the cells were seeded the media was supplemented with 3 mM β-glycerophospate and 10 μg/ml of L-ascorbic acid. The media was changed every other day and the cultures were incubated at 37° C. in a humidified atmosphere and 5% $CO_2$. Cells were cultured for a period of 28 days and data was collected on days 7, 14, 21, and 28.

Cell viability was measured using a Cell Titer 96™ Aqueous Solution Cell Proliferation Assay (MTS Assay) (Promega, Madison, Wis., USA) on the following scaffolds Min0 (n=6) and Min24 (n=6). At each time point (7, 14, 21, and 28 days) the media was removed, then 300 μl of fresh media and 60 μl of the MTS solution were added to each well and incubated at 37° C. with 5% $CO_2$ for three hours. After incubation, 300 μl of the mixture was transferred to a 48-well plate and diluted with 300 μl of di water. The plate was read at 490 nm using a plate reader. Calibration curve with known cell numbers was performed on the beginning of the study to correlate MTS absorbance values to cell numbers.

Osteocalcin ELISA Assay

Osteocalcin (OCN) is a non-collagenous protein produced by mature osteoblasts during later stages of differentiation. It was measured in the media using an ELISA kit from Biomedical Technologies, Inc (Stoughton, Mass.). Media samples (n=4) were collected over the course of 28 days and stored at −80° C. until the end of study. The assay was performed according to the manufactures instructions and absorbance was read at 450 nm. Osteocalcin content is expressed as ng/cell.

Alizarin Red and Fluorescence Stain

Mineral deposition and distribution were characterized by the alizarin red stain. At each time point, the scaffolds were washed with PBS and transferred into new well plates. The scaffolds were then fixed in 70% ethanol for 1 hr at 4° C. and stained with 40 mM Alizarin red solution for 10 min. The scaffolds were then washed with dI water five times, placed into cryo-molds, imbedded in OCT imbedding medium, and frozen at −20° C. The scaffolds were cut into 50 µm section using a Cryostat HM 550 (Thermo Scientific Microm, Walldorf, Germany), and imaged using a light microscope (Leica Microsystems LAS AF 6000, Bannockburn, Ill., USA).

Cellular attachment on the scaffolds was qualitatively observed by fluorescence staining. Scaffolds were fixed in 3.7% paraformaldehyde and 0.5% Triton X-100 at room temperatures and stained with phalloidin and DAPI. The scaffolds were imaged using a fluorescence microscope (Leica Microsystems, Bannockburn, Ill., USA).

Results

In this study we fabricated complete three dimensional electrospun scaffolds and mineralized then by incubation in 10×SBF. The scaffolds were composed of dual structures, an inner core surrounded by osteon-like scaffolds. The scaffolds were then further characterized to determine mechanical properties, mineral deposition and distribution, and cellular activity on the scaffolds.

Alizarin Red Staining

Mineral distribution across the scaffolds was observed using the alizarin red staining. After 6 hr of mineralization, minerals can be seen on the outer edges and on the osteons, but are absent from the central core. As the mineralization time increases more mineral can be seen on the scaffolds. After 24 and 48 hr scaffolds are completely covered in mineral and no differences can be seen between two mineralization times.

Mineral Ash Weights

Mineral ash weights were determined to quantify the amount of mineral present on the scaffolds. Increasing the mineralization time resulted in an increase mineral deposition, and each ash weight was significantly higher than those from previous time points.

Mechanical Properties

Scaffolds were tested under simulated physiological conditions in compression at a rate of 10% strain/min. Data was analyzed to determine yield stress and compressive modulus. No significant differences in mechanical properties were seen after 6 hr of mineralization and also between 24 hr and 48 hr of mineralization. Scaffolds mineralized for 24 hr and 48 hr had significantly higher yield stresses than scaffolds mineralized for 6 hr and 0 hr. Scaffolds mineralized for 24 hr had significantly higher compressive modulus than unmineral-ized scaffolds (0 hr).

Cell Study

Proliferation of the M3T3-E1 cells on the scaffolds was quantified using MTS assay on days 7, 14, 21, and 28 and the absorbances at 490 nm were recorded. Over the course of 4 weeks no differences were observed between the groups at any time point. Both groups did experience significant increases in absorbances over 28 days, Min0 group from day 7 to day 14 to day 21, and Min24 group from day 14 to day 21.

Osteocalcin ELISA Assay

Differentiation of osteoblasts was measured by the expression of osteocalcin over the course of the study. There was an increase in OCN secretion during the last two weeks of the study. Also, there was a significant increase in OCN secretion on mineralized scaffolds during days 18-20 and 25-27.

Alizarin Red and Fluorescence Stain

At each time point during the cell study, the scaffolds were fixed and stained with alizarin red to visualize mineral deposition and distribution. On day 0, prior to the start of the study, a small amount of mineral can be seen on Min0 scaffold from the premineralization treatment and a much greater amount of mineral can be seen on Min24 scaffolds. Over the course of study an increased amount of mineral can be seen both scaffold types, but overall Min24 scaffolds seem to have more mineral present.

Scaffolds were fluorescently stained to visualize cellular attachment and distribution on the scaffolds. Scaffold thickness and rough surfaces made focusing difficult. Cells can be seen on the edges of the scaffolds and also inside of the osteon channels.

Example 2

Fabrication of the fiber core (mimicking the trabecular section): poly L-lactic acid (PLLA) and gelatin nanofibers is electrospun with salt crystals, resulting in crystals embedded into the electrospun mat. A thin layer of poly D-L lactic acid nanofibers is electrospun onto the mat. The matrix is then crosslinked by exposure to 1-ethyl-3-[3-dimethylaminopropyl] carbodiimide hydrochloride (EDC). Salt crystals are removed by leaching, leaving behind pores. The large pores increase diffusion and cell infiltration within the scaffold. After salt removal, the resulting nanofibrous mat is be cut into circular shapes and then stacked and sintered into a cylinder at 54° C. for 40 min.

Fabrication of the fiber tubes (mimicking the cortical section): PLLA-gelatin and collagen nanofibers is electrospun as described above. The polymers are spun onto rotating polyethylene oxide (PEO) microfibers (diameter of 0.295±0.044 mm). A 0.25 ml of PDLLA is then electrospun onto the fibers and crosslinked. PEO is used because it is extremely water soluble. After crosslinking, the newly formed scaffolds is inserted into DI water for an hour to dissolve out the PEO fibers, leaving behind hollow tubes.

Fabrication of the supporting posts: Powdered hydroxyapatite is tightly packed in a cylindrical mold with water and held under a constant pressure of 44 MPa for 10 minutes. The columns is then sintered at 700° C. for 10 hours.

Fabrication of the scaffold: The fiber core is placed in the center of the scaffold, the fiber tubes and HAP supporting posts are placed around its circumference. The entire assembly is wrapped with a nanofibrous PDLA-PLLA sheet and placed into a mold with a controllable diameter to hold the device together during sintering (54° C. for 40 min). After sintering, the entire scaffold is mineralized in a specialized electric field mineralization chamber, which mineralizes the scaffold throughout the full thickness in much less time than normal static mineralization by using an electric field to force ions through the scaffold. The scaffold is mineralized for 8 hours under 5V, in simulated body fluid (changed every hour). The scaffold is mineralized to at least 30%. After mineralization the scaffold is evaluated for its physical and mechanical characteristics. HUVECs is then seeded inside the fiber tubes for 2 weeks to create organized neovessels. These vessels are then decellularized and the scaffold is sliced into 5 mm diameter by 2 mm thickness using a cryrotome. The scaffold is sterilized using ethylene oxide gas and autologous mouse BMSCs are seeded on to the scaffold one week prior to implantation.

The invention claimed is:

1. A scaffold for bone repair or regeneration comprising a fiber column, a plurality of fiber tubes, and a fiber core, wherein said fiber core is structurally different from said fiber tubes, said fiber tubers align around the circumference of said fiber core and are enclosed by said fiber column, and said fiber column, said fiber tubes and said fiber core comprise a biocompatible first polymer, and wherein said fiber tubes comprise hollow channels and said fiber core comprises pores.

2. The scaffold of claim 1, further comprising one or more supporting posts, said one or more cylindrical supporting posts prepared from a material selected from the group consisting of alpha tricalcium phosphate, beta tricalcium phosphate, and hydroxyapatite (HPA).

3. The scaffold of claim 1, wherein said fiber column, said fiber tubes, and fiber core each comprises a first polymer independently selected from the group consisting of polycarbonate, polymethylmethacrylate, polyethylene, polyurethane, polyaryl etherketone, polyetherether-ketone, polylactide, polyglycolide, poly(DL-lactide), poly(L-lactide), poly(glycolide), poly(ε-caprolactone), poly(dioxanone), poly(glyconate), poly(hydroxybutyrate), poly(hydroxyvalerate), poly(orthoesters), poly(carboxylates), poly(propylene fumarate), poly(phosphates), poly(anhy-drides), poly(iminocarbonates), poly(phosphazenes), and copolymers, blends and combinations thereof.

4. The scaffold of claim 3, wherein the first polymer comprises Poly (L-lactide) (PLLA).

5. The scaffold of claim 1, wherein said fiber column, said fiber tubes and said fiber core each comprises a cross-linked hydrogel independently selected from the group consisting of gelatin, alginic acid, hyaluronic acid, and poly(acrylic acid) hydrogel.

6. The scaffold of claim 5, wherein the cross-linked hydrogel comprises gelatin.

7. The scaffold of claim 1, wherein at least one of said fiber column, said fiber tubes, and said fiber core further comprises a second coating polymer.

8. The scaffold of claim 7, wherein the second coating polymer comprises Poly(D-lactide) (PDLA).

9. The scaffold of claim 1, further comprising a decellularized tissue in said fiber tubes.

10. The scaffold of claim 9, wherein the decellularized tissue comprises decellularized human umbilical vein endothelial cells (HUVEC).

11. The scaffold of claim 1, further comprising stem cells selected from the group consisting of mesenchymal stem cells (MSC), muscle-derived stem cells, and adipose derived stem cells.

12. The scaffold of claim 11, wherein the stem cells are MSC.

13. The scaffold of claim 1, wherein the fiber of the column aligns in an angle of between about 0 to 90 degrees along the longitudinal axis of the column.

14. The scaffold of claim 13, wherein the angle ranges from about 15 to about 45 degrees.

15. The scaffold of claim 13, wherein the angel is about 15 degrees.

16. The scaffold of claim 1, wherein the scaffold is mineralized.

17. The scaffold of claim 1, wherein the scaffold is heat sintered.

18. A method of fabricating a scaffold for bone repair or regeneration, comprising the steps of:
    a) surrounding a fiber core with a plurality of fiber tubes, wherein said fiber tubes comprise hollow channels and said fiber core comprises pores;
    b) enclosing the plurality of fiber tubes with a fiber sheet to form a column; and
    c) sintering the column.

19. The method of claim 18, further comprising placing one or more supporting posts around the fiber core in step a, said one or more supporting posts comprising HPA.

20. The method of claim 18, further comprising seeding a tissue in the fiber tubes and decellularizing the tissue.

21. The method of claim 18, further comprising seeding stem cells on to the scaffold.

22. The method of claim 18, further comprising mineralizing at least one of said fiber sheet, fiber core, or fiber tubes before sintering, after sintering, or both.

23. A method for bone replacement or repair comprising implanting the scaffold of claim 1 in a site in need of bone replacement or repair on a patient.

24. A method of implanting the scaffold of claim 1, comprising the steps of:
    a) creating a subcutaneous pocket on a patient; and
    b) placing the scaffold of claim 1 into the pocket.

25. The method of claim 24, further comprising seeding onto the scaffold stem cells prior to step a.

26. The scaffold of claim 1, further comprising one or more supporting posts distributed uniformly throughout a section where said fiber tubes are placed.

27. The scaffold of claim 1, further comprising one or more cylindrical supporting posts, said one or more supporting posts prepared from a polymer or mineral.

* * * * *

UNITED STATES PATENT AND TRADEMARK OFFICE
CERTIFICATE OF CORRECTION

PATENT NO. : 10,524,915 B2
APPLICATION NO. : 15/534857
DATED : January 7, 2020
INVENTOR(S) : Joseph W. Freeman et al.

Page 1 of 1

It is certified that error appears in the above-identified patent and that said Letters Patent is hereby corrected as shown below:

In the Specification

At Column 1, Line number 12, please enter the following:
STATEMENT REGARDING FEDERALLY SPONSORED RESEARCH
This invention was made with government support under grant number 0926970 awarded by the National Science Foundation. The government has certain rights in the invention.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*